(12) United States Patent
Chipman et al.

(10) Patent No.: US 7,235,677 B2
(45) Date of Patent: Jun. 26, 2007

(54) METHOD OF IMPROVING THE OPERATION OF AN EXISTING ETHYLENE OXIDE MANUFACTURING PROCESS AND SYSTEM

(75) Inventors: Peter Ingraham Chipman, Houston, TX (US); Ajay Madhav Madgavkar, Katy, TX (US); Gregg Barton Shipp, Katy, TX (US)

(73) Assignee: Shell Oil Company, Houston, TX (US)

( * ) Notice: Subject to any disclaimer, the term of this patent is extended or adjusted under 35 U.S.C. 154(b) by 509 days.

(21) Appl. No.: 10/789,052

(22) Filed: Feb. 27, 2004

(65) Prior Publication Data

US 2004/0171852 A1 Sep. 2, 2004

Related U.S. Application Data

(60) Provisional application No. 60/451,153, filed on Feb. 28, 2003.

(51) Int. Cl.
*C07D 301/10* (2006.01)
*C07D 301/08* (2006.01)

(52) U.S. Cl. .............. 549/536; 549/523; 549/534; 549/538

(58) Field of Classification Search ............ 549/536, 549/534, 523, 538
See application file for complete search history.

(56) References Cited

U.S. PATENT DOCUMENTS

| | | | | |
|---|---|---|---|---|
| 1,976,677 A | 10/1934 | Wittwer | ............ | 260/106 |
| 4,430,312 A | 2/1984 | Eickmeyer | ............ | 423/223 |
| 4,761,394 A | 8/1988 | Lauritzen | ............ | 502/348 |
| 4,766,105 A | 8/1988 | Lauritzen | ............ | 502/216 |
| 4,822,900 A | 4/1989 | Hayden | ............ | 549/534 |
| 4,831,162 A | 5/1989 | Nakajima et al. | ............ | 549/534 |
| 4,845,296 A | 7/1989 | Ahmed et al. | ............ | 564/477 |
| 5,145,658 A | 9/1992 | Chao | ............ | 423/232 |
| 5,187,140 A | 2/1993 | Thorsteinson et al. | ............ | 502/348 |
| 5,380,697 A | 1/1995 | Matusz et al. | ............ | 502/348 |
| 5,395,812 A | 3/1995 | Nagase et al. | ............ | 502/238 |
| 5,428,202 A | 6/1995 | Rossi | ............ | 219/110 |
| 5,597,773 A | 1/1997 | Evans et al. | ............ | 502/348 |
| 5,703,253 A | 12/1997 | Evans et al. | ............ | 549/536 |
| 5,840,932 A | 11/1998 | Evans et al. | ............ | 549/512 |
| 6,372,925 B1 | 4/2002 | Evans et al. | ............ | 549/536 |
| 6,452,027 B1 | 9/2002 | Billig et al. | ............ | 549/538 |
| 6,533,843 B2 | 3/2003 | Billig et al. | ............ | 95/172 |

FOREIGN PATENT DOCUMENTS

| | | |
|---|---|---|
| CA | 1180538 | 1/1985 |
| CA | 1286689 C | 7/1991 |
| EP | 266015 A | 5/1988 |
| EP | 393758 A | 10/1990 |
| EP | 425020 A | 5/1991 |
| EP | 480539 A | 4/1992 |
| EP | 557833 A | 9/1993 |
| EP | 393785 B1 | 1/1995 |
| GB | 2161480 A | 1/1986 |
| JP | 56005471 | 1/1981 |
| WO | WO-01/96324 | 12/2001 |

OTHER PUBLICATIONS

Brunauer. Emmet & Teller. J. Am. Chem. Soc. 60 (1938): pp. 309-316.
J. M. Kobe et al. Ency. Of Catalysis. vol. 3. I'T. Korrath (Ed.). p. 246. published Dec. 2002.
Intercom Article, p. 22. Apr. 2002. Workshop on Safety at SNR - Forum: 100 Years Shell Pernis (English translation provided).

*Primary Examiner*—Bernard Dentz (57) ABSTRACT

Described is a method of improving the process and operation of an existing system for manufacturing ethylene oxide. The ethylene oxide manufacturing system includes an epoxidation reactor system containing a volume of high activity epoxidation catalyst. The method includes replacing a portion of the volume of high activity epoxidation catalyst with a volume of high selectivity catalyst, and modifying the operation of the process system so as to provide for a feed to the epoxidation reactor system having a reduced carbon dioxide concentration.

38 Claims, 3 Drawing Sheets

METHOD OF IMPROVING THE OPERATION OF AN EXISTING ETHYLENE OXIDE MANUFACTURING PROCESS AND SYSTEM

This application claims the benefit of U.S. Provisional Application No. 60/451,153 filed Feb. 28, 2003 the entire disclosure of which is hereby incorporated by reference.

This invention relates to a process for manufacturing ethylene oxide. Another aspect of the invention relates to the improvement in the operation of an existing ethylene oxide manufacturing process by modifying the reactor system and the operation of the associated carbon dioxide removal system.

Prior to the discovery of high selectivity ethylene epoxidation catalysts used for the partial oxidation of ethylene to ethylene oxide and, even in some cases after the discovery of the high selectivity catalysts, ethylene oxide manufacturing process systems were designed for the use of high activity ethylene epoxidation catalysts. The use of high activity ethylene epoxidation catalysts provided for lower required reactor temperatures to achieve a given ethylene oxide production.

In recent years new highly selective catalysts have been developed that provide for selectivity benefits over the earlier developed high activity ethylene epoxidation catalysts. Such high selectivity catalysts are known from U.S. Pat. Nos. 4,761,394 and 4,766,105, which are incorporated herein by reference. However, due to their lower activity, the high selectivity catalysts employ higher reaction temperatures for a given ethylene oxide yield.

In certain circumstances benefits may be achieved by replacing the high activity catalyst of an ethylene manufacturing process system with a high selectivity catalyst; but, because the older ethylene manufacturing process systems usually have been designed for the use of the earlier generation of high activity catalysts, which require lower reaction temperatures, the high activity catalysts cannot simply be replaced with a high selectivity catalyst. For instance, the reactor system that is a part of an ethylene oxide manufacturing system is often designed for operating at lower reactor temperatures and, thus, is unable to operate at the higher temperatures that may be required with the use of a high selectivity epoxidation catalyst.

Accordingly, in ethylene oxide manufacturing process systems designed for the use of high activity epoxidation catalyst there is a need to provide for the replacement of the high activity catalyst with a high selectivity catalyst in order to exploit the benefits of such catalysts.

Other aspects, objects, and the several advantages of the invention will become apparent in light of the following disclosure.

According to the invention, a method is provided for improving the operation of an existing ethylene oxide manufacturing process. In this process, a first reactor feed, having a first carbon dioxide concentration, is charged to an epoxidation reactor system, which comprises an epoxidation reactor containing a first volume of high activity epoxidation catalyst. Yielded from the epoxidation reactor system is a first epoxidation reactor effluent. At least a portion of the first epoxidation reactor effluent is charged to an ethylene oxide absorber used for separating the first epoxidation reactor effluent into a first recycle stream, having a second carbon dioxide concentration, and a first ethylene oxide stream. The first recycle stream is split into a first split portion and a first remaining portion. A carbon dioxide removal system is provided which includes a carbon dioxide absorber and a solvent regenerator. The carbon dioxide absorber provides for receiving a carbon dioxide-containing feed gas and for contacting the carbon dioxide-containing feed gas with a lean solvent to yield a rich solvent and a carbon dioxide depleted gas stream, and the solvent regenerator provides for receiving the rich solvent and for separating carbon dioxide therefrom to yield the lean solvent and a carbon dioxide gas stream. At least a portion of the first remaining portion is charged to the carbon dioxide removal system as the carbon dioxide-containing feed gas to yield as the carbon dioxide depleted gas stream a second recycle stream, having a third carbon dioxide concentration, and to yield as the carbon dioxide gas stream a first carbon dioxide vent stream. At least a portion of the first split portion and at least a portion of the second recycle stream are combined with oxygen and ethylene to form the first reactor feed.

For improving the existing ethylene oxide manufacturing process in accordance with this invention, the process system is modified by removing from the epoxidation reactor at least a portion of the first volume of high activity epoxidation catalyst and replacing therewith a replacement charge of a second volume of a high selectivity epoxidation catalyst to provide a modified epoxidation reactor system. The modified epoxidation reactor system having the replacement charge is then charged with a second reactor feed having a fourth carbon dioxide concentration. Yielded from the modified epoxidation reactor system is a second epoxidation reactor effluent. At least a portion of the second epoxidation reactor effluent is charged to the ethylene oxide absorber used for separating the second epoxidation reactor effluent into a third recycle stream, having a fifth carbon dioxide concentration, and a second ethylene oxide stream. The third recycle stream is split into a second split portion, if any, and a second remaining portion. At least a portion of the second remaining portion is charged to the carbon dioxide removal system as the carbon dioxide-containing feed gas to yield as the carbon dioxide depleted gas stream a fourth recycle stream, having a sixth carbon dioxide concentration, and to yield as the carbon dioxide gas stream a second carbon dioxide vent stream. At least a portion of the second split portion, if any, and at least a portion of the fourth recycle stream are combined with oxygen and ethylene to form the second reactor feed.

A typical ethylene oxide manufacturing system, in general, comprises an epoxidation reactor system, an ethylene oxide recovery system, and a carbon dioxide removal system. These systems are operatively connected to each other so as to provide for the partial oxidation of ethylene with oxygen to yield ethylene oxide and the recovery of the ethylene oxide product. Carbon dioxide is an unwanted by-product of the epoxidation reaction and must be removed from the ethylene oxide manufacturing system at a rate that approximates its production in order to prevent its buildup in the system.

Usually, ethylene oxide manufacturing systems are designed with a certain type of epoxidation catalyst in mind and, before the advent of high selectivity catalysts, many ethylene manufacturing systems were designed for the use of high activity epoxidation catalysts. As it is used herein with reference to the selectivity of a catalyst, the term "selectivity", $S_w$, means the mole percent (%) of the desired ethylene oxide formed relative to the total of ethylene converted at a given work rate, w, for a catalyst with the work rate being defined as the amount of ethylene oxide produced per unit volume of catalyst (e.g., kg per m$^3$) per hour. As it is used herein with reference to the activity of a catalyst, the term "activity", $T_w$, means the temperature needed to reach a given work rate. Thus, a high activity epoxidation catalyst is a catalyst that employs a lower reaction temperature for a given ethylene oxide yield per quantity of epoxidation catalyst when compared to an alternative epoxidation catalyst. And, a high selectivity epoxidation catalyst is a catalyst that, for a given temperature, provides for a greater percentage of a converted feed that is converted to ethylene oxide product than an alternative epoxidation catalyst.

With the development of high selectivity catalysts, it has been found that in many circumstances there can be various economic and operating benefits to utilizing in the manufacture of ethylene oxide such high selectivity catalysts in place of high activity catalysts. In conventional ethylene oxide manufacturing systems designed to use high activity ethylene oxidation catalysts there can be great benefits to replacing the high activity catalyst with a high selectivity ethylene oxidation catalyst. But, because of the differences in the catalytic performance of the two types of catalysts, the design of an ethylene oxide manufacturing system that uses the high activity catalyst can be such as to prevent the simple replacement of the high activity catalyst with a high selectivity catalyst. Because the high activity catalyst typically employs a lower reactor temperature than does a high selectivity catalyst, the reactor system is often designed for lower operating temperatures and pressures. Also, the amount of carbon dioxide by-product yielded from an epoxidation reaction that uses a high activity catalyst, as opposed to one that uses a high selectivity catalyst, tends to be significantly higher. This results in higher carbon dioxide concentrations in the epoxidation reactor feed and in the epoxidation reactor effluent. These differences in carbon dioxide concentration can have an impact on the design and operation of the carbon dioxide removal system as well as on the epoxidation reaction and reactor system.

The inventive method contemplates improving the operation of an existing ethylene oxide manufacturing system that has been designed to use epoxidation catalysts that are highly active but generally less selective than some of the more recently developed highly selective epoxidation catalysts. In the ethylene oxide manufacturing system of the inventive method, the epoxidation reactor contains a first volume of high activity epoxidation catalyst. This first volume of high activity epoxidation catalyst is replaced, in part, or in whole, with a second volume of high selectivity catalyst.

While this higher selectivity catalyst provides for an increase in yield in ethylene oxide for a given ethylene feed with a reduced yield of carbon dioxide by-product, the higher selectivity catalyst is less active than the high activity catalyst therefore requiring a higher reactor temperature. These higher epoxidation reactor temperatures are often not achievable with the existing epoxidation reactor equipment due to various mechanical limitations designed into the systems that use the high activity catalyst.

It has been found, however, that in the use of high selectivity epoxidation catalysts in the manufacture of ethylene oxide by the partial oxidation of ethylene with oxygen at constant conversion or work rate the carbon dioxide concentration of the epoxidation reactor feed affects the catalyst selectivity and, by reducing the carbon dioxide concentration of the epoxidation reactor feed, significant reductions in reactor temperature can be achieved thereby allowing for the exploitation of the benefits provided by the replacement of the high activity catalyst with the high selectivity catalyst.

Thus, the inventive method can include, along with the removal of at least of a portion of the first volume of high activity catalyst of the epoxidation reactor and replacement therewith a second volume of high selectivity catalyst to give a modified epoxidation reactor system, modifications in the operation or equipment, or both, of the carbon dioxide removal system to provide for the ability to remove carbon dioxide from the ethylene oxide manufacturing process system so as to provide for the required lower carbon dioxide concentration in the epoxidation reactor feed.

After the high activity catalyst of the epoxidation reactor system has been replaced with a high selectivity catalyst, it is important for the carbon dioxide concentration of the reactor feed, comprising ethylene, oxygen and carbon dioxide, to be maintained at a low or at least a reduced concentration of, for example, less than about 3 mole percent based on the total moles of ethylene, oxygen, and carbon dioxide in the reactor feed. For best results, however, the carbon dioxide concentration of the reactor feed to the epoxidation reactor system containing a high selectivity catalyst should be less than about 2 mole percent, preferably less than about 1.5 mole percent and, most preferably, less than 1 mole percent based on the total moles of ethylene, oxygen, and carbon dioxide in the reactor feed. While it is most desirable for the concentration of carbon dioxide in the feed to the epoxidation reactor containing a high selectivity catalyst to be as low as is possible, there can be a practical lower limit and, thus, such lower limit can be about 0.1 mole percent of the ethylene, oxygen, and carbon dioxide of the reactor feed but, more likely, the lower limit is 0.2 mole percent or 0.3 mole percent.

To recover the ethylene oxide as a product, the epoxidation reactor effluent is charged to an ethylene oxide absorber used to separate the ethylene oxide from the epoxidation reactor effluent and to yield an ethylene oxide product stream that comprises ethylene oxide, and a gaseous recycle stream that comprises unreacted ethylene, unreacted oxygen, carbon dioxide and inert compounds. The ethylene oxide product can also include reaction by-products such as, for example, carboxylic acids (organic acids), aldehydes, carbon monoxide, and higher molecular weight hydrocarbons.

It is an important aspect of the invention for the carbon dioxide concentration of the epoxidation reactor effluent from the epoxidation reactor after replacement of the high activity catalyst with the high selectivity catalyst to be significantly lower than the carbon dioxide concentration before such replacement. The reduced carbon dioxide concentration of the epoxidation reactor effluent can be the result of several factors, including, for example, a modified operation of the carbon dioxide removal system and a lower carbon dioxide by-product yield resulting from the lower epoxidation reactor temperature due to the lower carbon dioxide epoxidation reactor feed concentration of the inventive process. The gaseous recycle stream from the ethylene oxide absorber after changing the high activity catalyst of the epoxidation reactor to a high selectivity catalyst will have a concentration of less than about 5 mole percent of the gaseous recycle stream. While it is best for this carbon dioxide concentration to be as low as is feasible, the carbon dioxide concentration of the gaseous recycle stream after the change in the epoxidation reactor catalyst to a high selectivity catalyst can generally be in the range of from about 1 mole percent to about 5 mole percent and, more specifically, it can range from 2 to 4 mole percent.

To remove carbon dioxide from the ethylene oxide manufacturing process system, the gaseous recycle stream may be divided into a split portion and a remaining portion with the split portion, if any, of the gaseous recycle stream being recycled back to the epoxidation reactor and the remaining portion of the gaseous recycle stream being charged to the carbon dioxide removal system.

The portion of the gaseous recycle stream recycled to the epoxidation reactor relative to the remaining portion of the recycle stream that is charged to the carbon dioxide removal system depends upon numerous factors, including, for example, the amount of by-product carbon dioxide produced in the epoxidation reaction and the efficiency of carbon dioxide recovery by the carbon dioxide removal system. After the change in the epoxidation catalyst of the epoxidation reactor from the high activity catalyst to the high selectivity catalyst, the inventive method requires the reduction of carbon dioxide concentration of the gaseous recycle stream that thereby creates a lower concentration driving force for the separation of carbon dioxide by the carbon dioxide removal system. Thus, the ratio of the portion of gaseous recycle stream to the remaining portion is reduced due to the need to charge more feed to the carbon dioxide removal system after the catalyst change. Accordingly, after the catalyst change the ratio of the remaining portion of the recycle stream charged to the carbon dioxide absorber to the total recycle stream yielding from the ethylene oxide absorber can generally be in the range of from about 0.3 upwardly to 1, but preferably, from about 0.4 to 1 and, most preferably, from 0.5 to 1.

The higher rate at which the remaining portion of gaseous recycle stream is charged to the carbon dioxide absorber can require a number of structural changes in the carbon dioxide absorber of the carbon dioxide removal system, such as, for example, modifying the internal structure of the carbon dioxide absorber so as to provide for greater contact surface area for contacting the lean solvent and carbon dioxide containing feed. For example, provided within the contacting zone defined by the carbon dioxide absorber can be a high surface area packing material so that the amount of contact surface area within the carbon dioxide absorber after the change in the epoxidation catalyst of the epoxidation reactor from a high activity to a high selectivity catalyst is greater than before such change. An alternative to changing the internal design of the existing carbon dioxide absorber is to provide one or more additional carbon dioxide absorbers, operatively connected in parallel with the existing absorber and capable of receiving as a carbon dioxide containing gaseous feed the remaining portion of the gaseous recycle stream.

The carbon dioxide removal system is a solvent extraction system that includes a carbon dioxide absorber and a solvent regenerator. A lean solvent is charged to the carbon dioxide absorber and is contacted with the remaining portion of gaseous recycle stream charged thereto. Yielded from the carbon dioxide absorber is a carbon dioxide rich solvent and a carbon dioxide depleted gaseous stream. The carbon dioxide depleted gaseous stream is recycled back to the epoxidation reactor where it is combined with the split portion of the gaseous recycle stream, oxygen, and ethylene to provide the epoxidation reactor feed.

While some carbon dioxide removal systems of existing ethylene oxide manufacturing process systems may be able to handle the increased demands that result from the modification of the epoxidation reactor system by changing the high activity catalyst with a high selectivity catalyst, many of carbon dioxide removal systems are unable to do so. Generally, as earlier noted herein, when the epoxidation reactor is modified by replacing the high activity catalyst with a high selectivity catalyst, the carbon dioxide concentration in the reactor feed needs to be lowered to achieve the greatest benefits from the use of the high selectivity catalyst. This requires a lower concentration of carbon dioxide in the recycle stream of the process thereby providing a smaller concentration differential between the feed to the carbon dioxide removal system and the extraction solvent which makes it more difficult to extract the carbon dioxide from the recycle stream.

In the carbon dioxide removal systems the absorption solvent used is an aqueous solution of an alkaline metal carbonate, for example, sodium carbonate and potassium carbonate. The inventive method contemplates modifying the solvent used in the carbon dioxide removal system of the invention by providing a concentration of an activator or catalyst in the lean solvent thereof. Such an activator or catalyst alters the mass transfer characteristics of the solvent so as to improve the absorption and desorption of carbon dioxide from the remaining portion of gaseous recycle charged to the carbon dioxide removal system. Potassium metavanadate is an example of one suitable activator that can be used as an additive to the solvent of the carbon dioxide removal system.

By modifying either the operation or structure of the carbon dioxide removal system the lower carbon dioxide concentration in the epoxidation reactor feed of the inventive method is obtained. The carbon dioxide concentration of the carbon dioxide depleted gaseous stream after the replacement of the high activity catalyst of the epoxidation reactor with the high selectivity catalyst can be less than about 2 mole percent of the total stream; however, it is an important aspect of the inventive method for the carbon dioxide concentration to be as low as is feasible, which is preferably less than about 1.5 mole percent and, more preferably, less than 1 mole percent. A typical range for the carbon dioxide concentration is from about 0.1 mole percent to about 2 mole percent, or from about 0.15 to about 1.75 mole percent, or from 0.2 to 1.5 mole percent.

The following Table 1 presents: exemplary carbon dioxide concentrations (mole percent) of various of the process streams of the ethylene oxide manufacturing process system before and after removing the high activity catalyst and replacing therewith a high selectivity catalyst.

TABLE 1

Exemplary Carbon Dioxide Concentrations (mole percent) of Various Streams of the Ethylene Oxide Manufacturing Process Before and After Catalyst Change

|  | Before | After |
| --- | --- | --- |
| Reactor Feed (% $CO_2$) | 4–20% | less than about 2% less than about 1.5% less than 1% |
| EO Absorber Recycle Gas (% $CO_2$) | 5–40% | less than 5% 1 to 5% 2 to 4% |
| $CO_2$ Absorber Recycle Gas (% $CO_2$) | 1–2% | less than about 2% less than about 1.5% less than 1% |

Both the high activity catalyst and the high selectivity catalyst that are referred to herein are supported silver-based catalysts, but the two catalysts, as earlier noted, have different catalytic performance characteristics.

The material of the supported silver-based catalysts can be selected from a wide range of porous support materials particularly those which are considered to be inert in the presence of the ethylene oxidation feeds, products and reaction conditions. Such materials can be natural or artificial, and they can include the aluminum oxides, magnesia, zirconia, silica, silicon carbide, clays, pumice, zeolites and charcoal. Alpha alumina is a preferred material for use as the main ingredient of the porous support.

The support material is porous and preferably has a surface area, as measured by the B.E.T. method, of less than 20 m$^2$/g and more in particular from 0.05 to 20 m$^2$/g. Preferably the B.E.T. surface area of the support is in the range of from 0.1 to 10, more preferably from 0.1 to 3.0 m$^2$/g. The B.E.T. method of measuring the surface area has been described in detail by Brunauer, Emmet and Teller in *J.Am.Chem.Soc.* 60 (1938) 309–316.

The highly selective supported silver-based catalyst of the invention is one which has an initial selectivity of at least 85%, preferably at least 86% and, most preferably, at least 87%. On the other hand, the initial selectivity of the highly active supported silver-based catalyst of the invention is one which has an initial selectivity that is less than the initial selectivity of the highly selective supported silver-based catalyst and, more specifically, the initial selectivity of the highly active supported silver-based catalyst is less than 85%. It is recognized, however, that from a practical standpoint the highly active catalyst will have some minimum selectivity. This minimum selectivity value is believed to be no lower than about 78%.

The term initial selectivity referred to herein means the selectivity of the given catalyst when it is fresh and unused. This recognizes that a catalyst can lose activity with use. The initial selectivity of a given catalyst is determined by measuring the selectivity of the catalyst using a standard testing procedure. In this standard testing procedure, a crushed catalyst (14–20 mesh) is placed within the ¼ inch diameter stainless steel U-tube of a micro-reactor operated under certain specified process conditions. A standard feed of 30 mole percent ethylene, 7 mole percent carbon dioxide, and 8.5 mole percent oxygen, and 54.5 mole percent nitrogen is introduced into the micro-reactor at a pressure of 210 psig and at such a rate as to provide a gaseous hourly space velocity of 3300 hr$^{-1}$. The selectivity, Sw, and activity, Tw, are determined for a work rate of 200 kg ethylene oxide yield per hour per cubic meter of catalyst. The selectivity is presented in terms of mole percent, and the activity is presented in terms of temperature in degrees centigrade.

In addition to the differences in the measured catalytic performances between the highly active and highly selective catalysts there also can be differences in the types and amounts of catalytic promoter compounds used in the two catalysts. One difference is that the high selectivity catalysts of the invention include a rhenium promoter component, whereas, on the other hand, the high activity catalysts contain, if any, an insignificant or nonpromoting amount of a rhenium component. Also, in addition to the rhenium component, the high selectivity catalysts can further contain a promoting amount of an alkali metal promoter or a further metal promoter, or both. Suitable high selectivity catalysts are described in detail in U.S. Pat. Nos. 4,761,394 and 4,766,105, which are incorporated herein by reference.

The high selectivity catalysts, thus, comprise a support material, a catalytically effective amount of silver, a promoting amount of rhenium and, optionally, a promoting amount of one or more alkali metals and, optionally, a promoting amount of one or more additional promoter metals. The amount of silver in the high selectivity catalyst can be in the range of from a catalytically effective amount upwardly to about 40 percent by weight of the total catalyst. Preferably, the amount of silver can range from about 1 to about 30 weight percent based on the total weight of the catalyst and, most preferably, from 5 to 20 weight percent.

The amount of rhenium in the high selectivity catalyst is a promoting amount generally ranging from a promoting amount upwardly to 20 micromoles of rhenium per gram of catalyst. The preferred amount of rhenium in the high selectivity catalyst ranges from about 0.1 micromoles per gram to about 10 micromoles per gram, more preferably from about 0.2 micromoles per gram to about 5 micromoles per gram of total catalyst, or, alternatively stated, from about 19 parts per million to about 1860 parts per million, preferably from about 37 parts per million to about 930 parts per million by weight of total catalyst.

The amount of alkali metal in the high selectivity catalyst, if any, is a promoting amount, generally ranging from a promoting amount upwardly to about 4000 parts per million by weight of the total catalyst (ppmw). Preferably, the amount of alkali metal, when present, is in the range of from about 10 to about 3000 ppmw, more preferably, from about 15 to about 2000 ppmw and, even more preferably, from 20 to 1500 ppmw.

The optional additional metal promoter of the high selectivity catalyst can be selected from the group of metals consisting of sulfur, molybdenum, tungsten, chromium, and mixtures of two or more thereof. The amount of additional metal promoters in the high selectivity catalyst, if any, is generally in the range of from about 0.1 to about 10 millimoles per kilogram of total catalyst, and, preferably, from 0.2 to 5 millimoles per kilogram of total catalyst.

As for the high activity catalyst, in addition to it being different from the high selectivity catalyst by exhibiting a lower selectivity as described above, it ordinarily does not contain a rhenium promoter, but it can contain one or more alkali metal promoters. Thus, the high activity catalyst preferably can comprise a support material, a catalytically effective amount of silver and a promoting amount of alkali metal but excluding a promoting amount of rhenium. Thus, the high activity catalyst can also consist essentially of a catalytically effective amount of silver, a promoting amount of alkali metal and a support material. Examples of suitable high activity catalysts are described in U.S. Pat. No. 5,380,697, which is incorporated herein by reference.

The silver component can be present in the high activity catalyst in the range of from a catalytically effective amount to about 40 weight percent based on the total weight of the catalyst. Preferably, however, the silver is present in the range of from about 1 to about 30 weight percent and, most preferably, from 5 to 20 weight percent.

The alkali metal component can be present in the high activity catalyst in the range of from a promoting amount upwardly to about 4000 ppmw. Preferably, alkali metal is present in the range of from 10 to 3000 ppmw and, more preferably, from 15 to 2000 ppmw.

Suitable epoxidation reaction conditions of the inventive method can include a reactor temperature in the range of from about 180° C. to about 320° C., but it is recognized that the inventive method permits the operation of the epoxidation reactor zone at lower temperatures without loss in the selectivity of the high selectivity catalyst. Indeed, the lower operating reaction temperature provided by the inventive process results in the enhancement in the life of the high activity catalyst and, thus, an improvement in the economic efficiency of the ethylene oxide manufacturing process. A more preferred range for the reactor temperature is from 190° C. to 310° C. and, most preferred, it is from 200° C. to 300° C. The preferred reaction pressure is from atmospheric upwardly to 35 bar. The preferred gaseous hourly space velocity is in the range of from about 1500 $hr^{-1}$ to 10,000 $hr^{-1}$.

Figure 1:
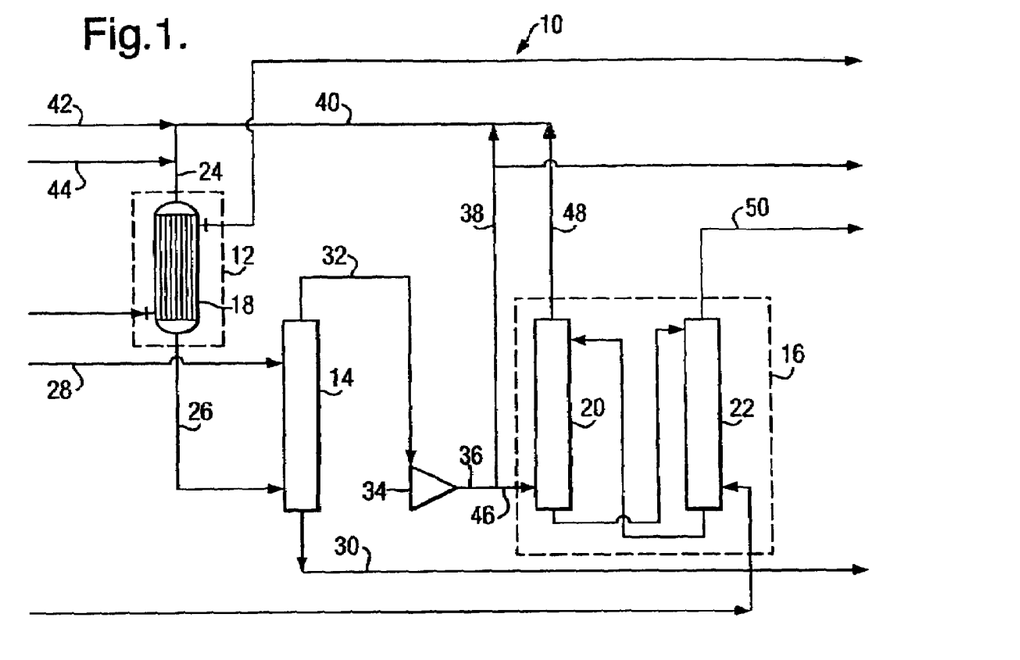
FIG. 1 is a schematic representation of an ethylene oxide manufacturing process system.

Now referring to FIG. 1, wherein is presented a schematic representation of an ethylene oxide manufacturing process system 10, which includes epoxidation reactor system 12, ethylene oxide recovery system or ethylene oxide absorber 14, and carbon dioxide removal system 16. Epoxidation reactor system 12 includes epoxidation reactor 18, which provides means for contacting a feed stream containing oxygen, ethylene and carbon dioxide with an epoxidation catalyst under suitable epoxidation reaction conditions to thereby yield ethylene oxide. Epoxidation reactor 18 defines an epoxidation reaction zone and contains a first volume of high activity epoxidation catalyst.

The carbon dioxide removal system 16 includes carbon dioxide absorber 20 and solvent regenerator 22. Carbon dioxide absorber 20 defines a carbon dioxide absorption zone and provides means for receiving a carbon dioxide containing gaseous feed with a lean solvent so as to yield a rich solvent, containing carbon dioxide, and a carbon dioxide depleted gas stream. Solvent regenerator 22 defines a solvent regeneration zone and provides means for separating carbon dioxide from the rich solvent so as to yield a carbon dioxide stream and the lean solvent, which is used as a feed to carbon dioxide absorber 20.

In the operation of an ethylene oxide manufacturing process system 10 that is designed for the use of a high activity epoxidation catalyst a first reactor feed, having a first carbon dioxide concentration, is charged to epoxidation reactor 18 through conduit 24 where within epoxidation reactor 18 the first reactor feed is contacted under suitable epoxidation reaction conditions with the high activity epoxidation catalyst. A first epoxidation reactor effluent is yielded from epoxidation reactor 18 of the epoxidation reactor system 12 and is charged to ethylene oxide absorber 14 via conduit 26. Ethylene oxide absorber 14 defines an ethylene oxide absorption zone and provides means for contacting an absorption solvent, such as water, with the first epoxidation reactor effluent and to yield a first recycle stream and a first ethylene oxide stream. The absorption solvent is introduced into ethylene oxide absorber 14 by way of conduit 28 where within ethylene oxide absorber 14 it is contacted with the first epoxidation reactor effluent. A first ethylene oxide stream, comprising the absorption solvent and ethylene oxide, passes from ethylene oxide absorber 14 by way of conduit 30 and a first recycle stream, having a second carbon dioxide concentration, passes from ethylene oxide absorber 14 by way of conduit 32 to recycle compressor 34. In addition to the carbon dioxide contained in the first recycle stream it also can comprise ethylene, oxygen, and inert compounds.

Recycle compressor 34 defines a compression zone and provides means for compressing the first recycle stream. The discharge of the compressed first recycle stream passes from recycle compressor 34 through conduit 36. A first split portion of the compressed first recycle stream passes by way of conduit 38 and then conduit 40 where it is combined with oxygen introduced by way of conduit 42 and ethylene introduced by way of conduit 44.

The remaining portion of the compressed first recycle stream is charged to carbon dioxide absorber 20 of carbon dioxide removal system 16 by way of conduit 46 as the carbon dioxide containing gaseous feed. Yielded by way of conduit 48, as the carbon dioxide depleted gas stream, is a second recycle stream, having a third carbon dioxide concentration. The second recycle stream passes to conduit 40 where it is further combined with the first split portion of the compressed first recycle stream, oxygen, and ethylene respectively introduced into conduit 40 through conduits 38, 42 and 44. The combination of these streams form the first reactor feed charged to epoxidation reactor 18 by way of conduit 24. A first carbon dioxide vent stream, comprising carbon dioxide, is yielded as the carbon dioxide stream from solvent regenerator 22 of the carbon dioxide removal system 16 through conduit 50.

Figure 2:
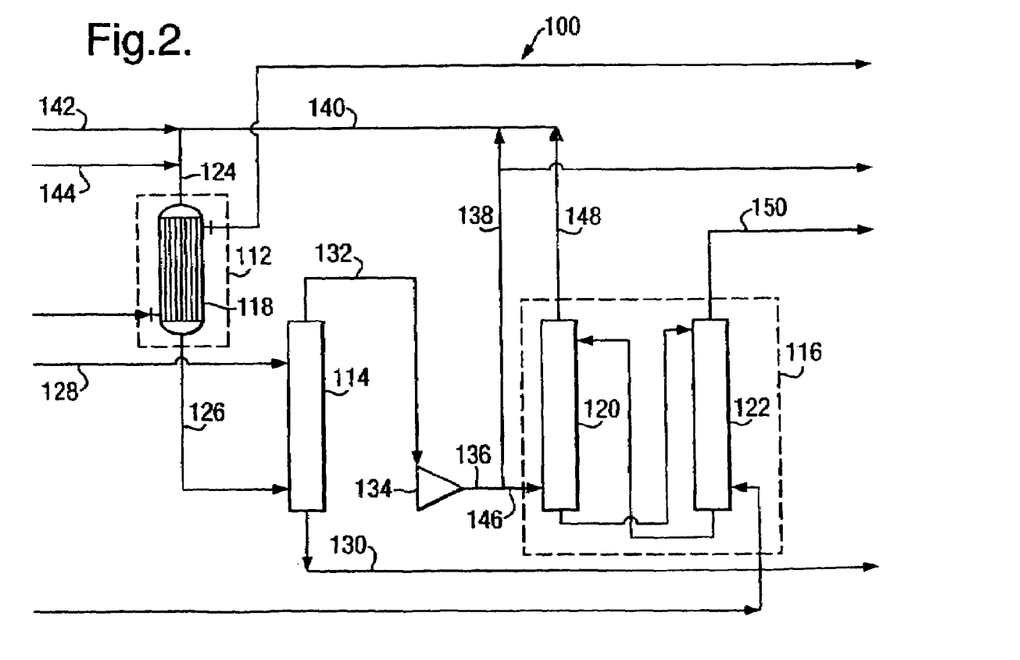
FIG. 2 is a schematic representation of the ethylene oxide manufacturing process system of FIG. 1 with a modified epoxidation reaction system.

Now referring to FIG. 2, which depicts an ethylene oxide manufacturing system 100, modified in accordance with this invention. To improve the operation of the ethylene oxide manufacturing process system 10 of FIG. 1 the epoxidation reactor system 12 therein is modified by removing at least a portion of the first volume of high activity catalyst contained in epoxidation reactor 18 and replacing therewith a second volume of a high selectivity catalyst to give modified epoxidation reactor system 112 with modified epoxidation reactor 118 both as shown in FIG. 2. In order to perform this catalyst replacement, the first reactor feed to epoxidation reactor 18 is stopped so as to permit catalyst removal and replacement thereof.

After the removal of the high activity catalyst from epoxidation reactor 18 and replacement therewith a high selectivity catalyst, a second reactor feed, having a fourth carbon dioxide concentration, is charged to epoxidation reactor 118 of the modified epoxidation reactor system 112 through conduit 124. Within epoxidation reactor 118 the second reactor feed is contacted under suitable epoxidation reaction conditions with the high selectivity epoxidation catalyst.

A second epoxidation reactor effluent is yielded from epoxidation reactor 118 of the modified epoxidation reactor system 112 and is charged to ethylene oxide absorber 114 via conduit 126. Ethylene oxide absorber 114 defines an ethylene oxide absorption zone and provides means for contacting an absorption solvent, such as water, with the second epoxidation reactor effluent and to yield a third recycle stream and a second ethylene oxide stream. The absorption solvent is introduced into ethylene oxide absorber 114 by way of conduit 128 where within ethylene oxide absorber 114 it is contacted with the second epoxidation reactor effluent. A second ethylene oxide stream, comprising the absorption solvent and ethylene oxide, passes from ethylene oxide absorber 114 by way of conduit 130 and a third recycle stream, having a fifth carbon dioxide concentration, passes from ethylene oxide absorber 114 by way of conduit 132 to recycle compressor 134. In addition to the carbon dioxide contained in the third recycle stream it also can comprise ethylene, oxygen, and inert compounds.

Recycle compressor 134 defines a compression zone and provides means for compressing the third recycle stream. The discharge of the compressed third recycle stream passes through conduit 136. A second split portion, if any, of the compressed third recycle stream passes by way of conduit 138 and then conduit 140 where it is combined with oxygen introduced by way of conduit 142 and ethylene introduced by way of conduit 144.

The remaining portion of the compressed third recycle stream is charged to carbon dioxide absorber 120 of carbon dioxide removal system 116 by way of conduit 146 as the carbon dioxide containing gaseous feed. Yielded by way of conduit 148 as the carbon dioxide depleted gas stream is a fourth recycle stream, having a sixth carbon dioxide concentration. The fourth recycle stream passes to conduit 140 where it is further combined with the second split portion of the compressed third recycle stream, oxygen, and ethylene respectively introduced into conduit 140 through conduits 138, 142 and 144. The combination of these streams form the second reactor feed charged to epoxidation reactor 118 by way of conduit 124. A second carbon dioxide vent stream, comprising carbon dioxide, is yielded as the carbon dioxide stream from solvent regenerator 122 of the carbon dioxide removal system 116 through conduit 150.

The following Examples 1 and 2 are intended to illustrate certain of the advantages of the use of a high selectivity catalyst under the conditions of a relatively low carbon dioxide concentration in the epoxidation feed. The following Example 3 is intended to illustrate certain of the advantages of the present invention and is not intended to unduly limit the scope of the invention.

EXAMPLE 1

A high selectivity catalyst, containing silver and promoting amounts of rhenium, lithium, cesium and sulfur on alpha-alumina was tested in the production of ethylene oxide from ethylene and oxygen. To do this, a sample of crushed catalyst was loaded into a stainless steel U-shaped reactor tube. The tube was immersed in a molten metal bath (heat medium) at 180° C., and the ends of the tube were connected to a gas flow system. A gas mixture passed through the catalyst bed, in a "once-through" operation. The weight of catalyst used and the inlet gas flow rate were adjusted to give a gas hourly space velocity of 3300 Nl/(l.h). The inlet gas pressure was 1550 kPa absolute.

The composition of the gas mixture was adjusted to 30 volume percent ethylene, 8 volume percent oxygen, 1 volume percent carbon dioxide, 2.5 parts per million by volume (ppmv) ethyl chloride, and nitrogen balance.

The temperature of the catalyst bed was ramped up at a rate of 10° C. per hour to 225° C. and then the temperature was adjusted so as to achieve an oxygen conversion of 40 mole percent. The ethyl chloride concentration in the gas mixture was adjusted to 2.5 ppmv so as to obtain an optimum selectivity of ethylene oxide formation. The activity of the catalyst is expressed as the temperature at which a 40 mole percent oxygen conversion is achieved (T40); the selectivity is the selectivity at the temperature T40. During the run the catalyst was subject to degradation, and in order to maintain a constant 40 mole percent oxygen conversion the temperature was gradually increased. The results are given in TABLE 2.

In three similar comparative tests, the concentration of carbon dioxide in the gas mixture was 5 to 7 percent volume, instead of 1 percent volume. The average result of the three comparative tests is also given in TABLE 2.

TABLE 2

| $CO_2$ concentration, % v | 1 | 5–7 |
|---|---|---|
| Run time, days | 263 | 195 |
| T40, initial, ° C. | 248 | 261 |
| Average activity decline rate, ° C./month | 2.1 | 2.9 |
| Initial selectivity, % mole | 86.0 | 85.1 |
| Average selectivity decline rate, % mole/month | 0.7 | 1.1 |

T40: temperature at 40% mole oxygen conversion

The results in TABLE 2 show clearly that a lower carbon dioxide concentration in the epoxidation reactor feed improves the performance of a high selectivity catalyst, in respect of its activity, selectivity and catalyst life.

EXAMPLE 2

This calculated example presents data generated by a proprietary model for predicting the performance of a high selectivity epoxidation catalyst at the operating conditions of an hourly space velocity of 4700 GSHV, a pressure of 21.7 barg, and a work rate of 184 kg/m³/hr for a reactor feed containing 25 mole percent ethylene and 8 mole percent oxygen. The model is based on the correlation of actual catalyst performance data gathered from numerous sources such as micro-reactor activity data, pilot plant data and other sources of catalyst performance data.

Figure 3:
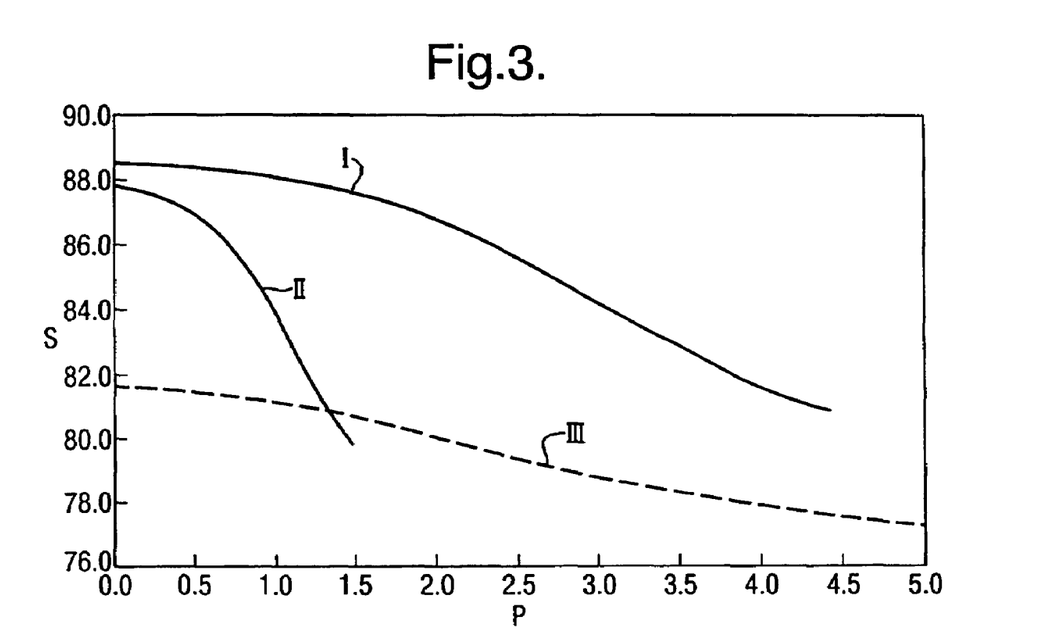
FIG. 3 demonstrates the improvement in catalytic life and selectivity of a high selectivity catalyst with plots of catalyst selectivity ("S", in %), at a given work rate, as a function of cumulative ethylene oxide production ("P", in $kton/m^3$) for the use of a high selectivity epoxidation catalyst ("I") under conditions of a relatively low carbon dioxide concentration in the epoxidation feed as compared to the conventional use of a high selectivity epoxidation catalyst ("II") and the conventional use of a high activity catalyst ("III")
Figure 5:
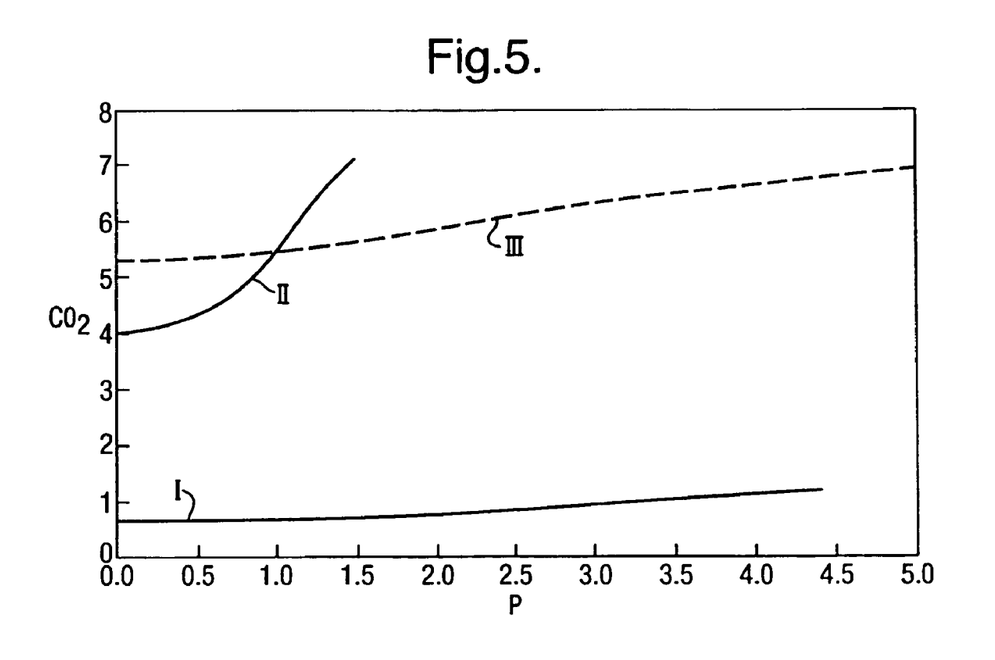
FIG. 5 presents plots of the reactor inlet concentration of carbon dioxide ("$CO_2$", in mole %) as a function of the cumulative ethylene oxide production ("P", in kton/m$^3$) corresponding to the values for selectivity and reactor coolant temperature presented in FIG. 3 and FIG. 4.

FIG. 3 presents the selectivity of a high selectivity epoxidation catalyst as a function of the age of the catalyst based on the cumulative ethylene oxide production in kton/m³ for the corresponding feedstock carbon dioxide concentrations presented in FIG. 5. The plots show that there is a strong relationship between catalyst life and feedstock carbon dioxide concentration and between selectivity and feedstock carbon dioxide concentration. As is shown in FIG. 3, the rate of decline in the selectivity of the catalyst when processing a feedstock having a carbon dioxide concentration of less than about 1 mole percent (curve marked "I") is significantly lower than the rate of decline in the selectivity of the catalyst when processing a feedstock having a more conventional carbon dioxide concentration of greater than about 4 mole percent (curve marked "II"). It is also noted that the initial selectivity of the high selectivity catalyst is higher for the case in which the feedstock has a carbon dioxide concentration of less than about 1 mole percent as opposed to a feedstock carbon dioxide concentration of greater than 4 mole percent. These data demonstrate the great benefits in the selectivity and life of a high selectivity epoxidation catalyst that are obtainable from processing an epoxidation reactor feedstock having a low carbon dioxide concentration. Further comparative data relate to the use of a high activity catalyst operated at greater than 4 mole percent carbon dioxide concentration (curve marked "III").

Figure 4:
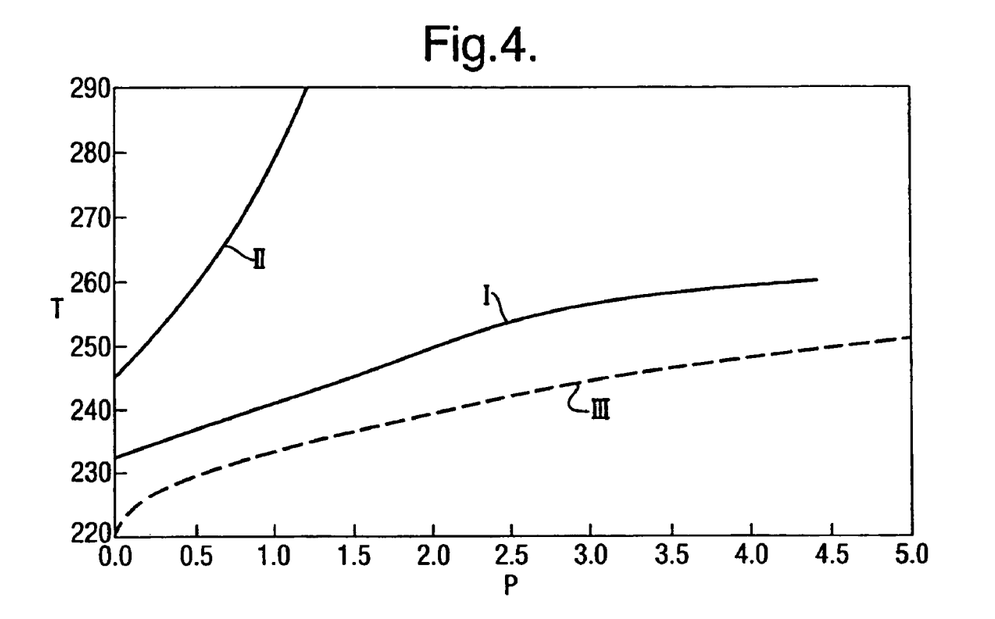
FIG. 4 demonstrates the improvement in catalytic life and reaction temperature with plots of reactor coolant temperature ("T", in °C.) as a function of cumulative ethylene oxide production ("P", in $kton/m^3$) for the use of a high selectivity epoxidation catalyst ("I") under conditions of a relatively low carbon dioxide concentration in the epoxidation feed as compared to the conventional use of high selectivity epoxidation catalyst ("II") and the conventional use of a high activity catalyst ("III")

FIG. 4 presents the reactor coolant temperature as a function of the age of the catalyst used in the epoxidation reaction for the corresponding feedstock carbon dioxide concentrations presented in FIG. 5. The reactor coolant temperature approximates the reaction temperature. As the data demonstrate, the epoxidation catalyst of the inventive method that processes an epoxidation reactor feedstock having a low carbon dioxide concentration of less than about 1 mole percent (curve marked "I") loses its activity at significantly lower rate than the epoxidation catalyst of the conventional method that processes an epoxidation reactor feedstock having a significantly higher concentration of carbon dioxide than that of the inventive method (curve marked "II"). These data show that the stability of the high selectivity epoxidation catalyst in terms of the rate of decline in catalyst activity is significantly improved with the inventive method which includes the processing of an epoxidation feedstock having a very low carbon dioxide concentration. Further comparative data relate to the use of a high activity catalyst operated at greater than 4 mole percent carbon dioxide concentration (curve marked "III").

EXAMPLE 3

This calculated example presents selected information concerning the carbon dioxide concentrations of several of the streams for the operation of a hypothetical 800 ton per day ethylene oxide manufacturing process system that uses a high activity epoxidation catalyst and for the operation of the same process system after such high activity epoxidation catalyst has been replaced with a high selectivity epoxidation catalyst. Also presented are the ratios of the quantity of feedstock charged to the process system after the catalyst change and before the catalyst change, and presented is the ratio of ethylene oxide yield after the catalyst change and before the catalyst change. The data presented are based on the output of a proprietary process model of the hypothetical ethylene oxide manufacturing process system. Assumed in the calculations for the process system using the high selectivity catalyst is the charging of 100 percent of the ethylene oxide absorber recycle stream to the carbon dioxide removal system, and for the process system using the high activity catalyst, 25 percent of the ethylene oxide absorber recycle stream is assumed to be charged to the carbon dioxide removal system.

TABLE 3

Carbon Dioxide Concentrations of Various Streams Before and After Catalyst Change (numbers in brackets refer to the corresponding numbers in FIG. 1 and FIG. 2)

| Stream | Concentration | $CO_2$ Concentration (mole %) |
|---|---|---|
| Reactor Feed | | |
| First reactor feed (24) | 1st $CO_2$ conc. | 5.32 |
| Second rector feed (124) | 4th $CO_2$ conc. | 0.65 |
| Recycle Stream | | |
| First recycle stream (32) | 2nd $CO_2$ conc. | 6.5 |
| Third recycle stream (132) | 5th $CO_2$ conc. | 1.2 |
| $CO_2$ Depleted Recycle Stream | | |
| Second recycle stream (48) | 3rd $CO_2$ conc. | 1.0 |
| Fourth recycle stream (148) | 6th $CO_2$ conc. | 0.7 |

TABLE 4

Ratio of Certain Feed and Product Stream Rates Relative to Such Rates Before Catalyst Change (numbers in brackets refer to the corresponding numbers in FIG. 1 and FIG. 2)

| | Ratio (After/Before) |
|---|---|
| Ethylene Feed (144)/(44) | 0.921 |
| Oxygen Feed (142)/(42) | 0.758 |
| Ethylene Oxide* Yield (130)/(30) | 1.000 |

*Ethylene Oxide only, excluding solvent and other components.

The data presented in the above TABLES 3 and 4 show that the inventive method provides for a significant improvement in the efficiency of the ethylene oxide manufacturing system. For a given ethylene oxide production there is large reduction in the amount of feedstock consumed in its manufacture. The consumption of ethylene feed is reduced by 7.9 percent and the consumption of oxygen feed is reduced by 24.2 percent. These reductions in feedstock consumption provide huge economic benefits that result from the inventive method.

While this invention has been described in terms of the presently preferred embodiment, reasonable variations and modifications are possible by those skilled in the art. Such variations and modifications are within the scope of the described invention and the appended claims.

That which is claimed is:

1. A method of improving the operation of an existing ethylene oxide manufacturing process, said method comprises:

a.) operating an epoxidation reactor system by:
charging a first reactor feed, having a first carbon dioxide concentration, to said epoxidation reactor system comprising an epoxidation reactor containing a first volume of high activity epoxidation catalyst;
yielding from said epoxidation reactor system a first epoxidation reactor effluent;
charging at least a portion of said first epoxidation reactor effluent to an ethylene oxide absorber used for separating said first epoxidation reactor effluent into a first recycle stream, having a second carbon dioxide concentration, and a first ethylene oxide stream;
dividing said first recycle stream into a first split portion and a first remaining portion;
providing a carbon dioxide removal system which includes a carbon dioxide absorber and a solvent regenerator, wherein said carbon dioxide absorber provides for receiving a carbon dioxide-containing feed gas and for contacting said carbon dioxide-containing feed gas with a lean solvent to yield a rich solvent and a carbon dioxide depleted gas stream, and wherein said solvent regenerator provides for receiving said rich solvent and separating carbon dioxide therefrom and yielding said lean solvent and a carbon dioxide gas stream;
charging at least a portion of said first remaining portion to said carbon dioxide removal system as said carbon dioxide-containing feed gas to yield as said carbon dioxide depleted gas stream a second recycle stream, having a third carbon dioxide concentration, and to yield as said carbon dioxide gas stream a first carbon dioxide vent stream;

combining at least a portion of said first split portion and at least a portion of said second recycle stream with oxygen and ethylene to thereby form said first reactor feed;

b.) replacing at least a portion of said first volume of high activity epoxidation catalyst by:

removing from said epoxidation reactor at least a portion of said first volume of high activity epoxidation catalyst and replacing therewith a replacement charge of a second volume of a high selectivity epoxidation catalyst to provide a modified epoxidation reactor system;

c.) operating said modified epoxidation reactor system by:

charging a second reactor feed, having a fourth carbon dioxide concentration which is lower than said first carbon dioxide concentration, to said modified epoxidation reactor system having said replacement charge;

yielding from said modified epoxidation reactor system a second epoxidation reactor effluent;

charging at least a portion of said second epoxidation reactor effluent to said ethylene oxide absorber used for separating said second epoxidation reactor effluent into a third recycle stream, having a fifth carbon dioxide concentration, and a second ethylene oxide stream;

dividing said third recycle stream into a second split portion, if any, and a second remaining portion;

charging at least a portion of said second remaining portion to said carbon dioxide removal system as said carbon dioxide-containing feed gas to yield as said carbon dioxide depleted gas stream a fourth recycle stream, having a sixth carbon dioxide concentration, and to yield as said carbon dioxide gas stream a second carbon dioxide vent stream; and combining at least a portion of said second split portion, if any, and at least a portion of said fourth recycle stream with oxygen and ethylene to thereby form said second reactor feed.

2. A method as recited in claim 1, wherein said lean solvent comprises an aqueous solution of alkali metal carbonate.

3. A method as recited in claim 2, further comprising adding an activator to said aqueous solution of alkali metal carbonate.

4. A method as recited in claim 3, further comprising: providing a second carbon dioxide absorber operatively connected in parallel with said carbon dioxide absorber wherein said second carbon dioxide absorber is capable of receiving at least a portion of said second remaining portion and contacting therewith said lean solvent to thereby provide at least a portion of said fourth recycle stream.

5. A method as recited in claim 3, further comprising: modifying the internals of said carbon dioxide absorber to thereby provide enhanced mass transfer and a greater number of theoretical trays and to improve the recovery of carbon dioxide from said at least a portion of said second split portion.

6. A method as recited in claim 3, further comprising: operating said carbon dioxide absorber so as to provide a fourth carbon dioxide concentration less than said first carbon dioxide concentration.

7. A method as recited in claim 1, wherein the fourth carbon dioxide concentration is less than 3 mole percent, based on the total moles of ethylene, oxygen and carbon dioxide in the reactor feed.

8. A method as recited in claim 7, wherein the fourth carbon dioxide concentration is in the range of from 0.1 to less than 2 mole percent, based on the total moles of ethylene, oxygen and carbon dioxide in the reactor feed.

9. A method as recited in claim 8, wherein the fourth carbon dioxide concentration is in the range of from 0.2 to less than 1.5 mole percent, based on the total moles of ethylene, oxygen and carbon dioxide in the reactor feed.

10. A method as recited in claim 1, wherein the high selectivity epoxidation catalyst is a silver-based catalyst which includes a rhenium promoter component, and the high activity catalyst is a silver-based catalyst that does not contain a rhenium promoter component, or contains a nonpromoting amount of a rhenium component.

11. A method as recited in claim 10, wherein the high selectivity epoxidation catalyst comprises as a support material an alpha alumina, the amount of silver is in the range of from 1 to 40 weight percent, and the amount of rhenium is in the range of from 0.1 to 10 micromoles per gram, based on the total weight of catalyst; and wherein the high activity catalyst comprises as a support material an alpha alumina, and the amount of silver is in the range of from 1 to 40 weight percent, based on the total weight of catalyst.

12. A method as recited in claim 1, wherein said first reactor feed comprises ethylene and oxygen, in addition to a concentration of carbon dioxide, and said second reactor feed comprises ethylene and oxygen, in addition to a concentration of carbon dioxide.

13. A process for manufacturing ethylene oxide, comprising manufacturing ethylene oxide by operating an ethylene oxide manufacturing process which has been improved by a method as recited in claim 1.

14. A method of improving the operation of an existing ethylene oxide manufacturing process, said method comprises:

a.) operating an epoxidation reactor system by:

charging a first reactor feed, having a first carbon dioxide concentration, to said epoxidation reactor system comprising an epoxidation reactor containing a first volume of a silver-based catalyst that does not contain a rhenium promoter component, or contains a nonpromoting amount of a rhenium component;

yielding from said epoxidation reactor system a first epoxidation reactor effluent;

charging at least a portion of said first epoxidation reactor effluent to an ethylene oxide absorber used for separating said first epoxidation reactor effluent into a first recycle stream, having a second carbon dioxide concentration, and a first ethylene oxide stream;

dividing said first recycle stream into a first split portion and a first remaining portion;

providing a carbon dioxide removal system which includes a carbon dioxide absorber and a solvent regenerator, wherein said carbon dioxide absorber provides for receiving a carbon dioxide-containing feed gas and for contacting said carbon dioxide-containing feed gas with a lean solvent to yield a rich solvent and a carbon dioxide depleted gas stream, and wherein said solvent regenerator provides for receiving said rich solvent and separating carbon dioxide therefrom and yielding said lean solvent and a carbon dioxide gas stream;

charging at least a portion of said first remaining portion to said carbon dioxide removal system as said carbon dioxide-containing feed gas to yield as said carbon dioxide depleted gas stream a second recycle stream, having a third carbon dioxide concentration, and to yield as said carbon dioxide gas stream a first carbon dioxide vent stream;

combining at least a portion of said first split portion and at least a portion of said second recycle stream with oxygen and ethylene to thereby form said first reactor feed;

b.) replacing at least a portion of said first volume of silver-based catalyst by:

removing from said epoxidation reactor at least a portion of said first volume of said silver-based catalyst that does not contain a rhenium promoter component, or contains a nonpromoting amount of a rhenium component, and replacing therewith a replacement charge of a second volume of a silver-based catalyst which includes a rhenium promoter component, to provide a modified epoxidation reactor system;

c.) operating said modified epoxidation reactor system by:

charging a second reactor feed, having a fourth carbon dioxide concentration which is lower than said first carbon dioxide concentration, to said modified epoxidation reactor system having said replacement charge;

yielding from said modified epoxidation reactor system a second epoxidation reactor effluent;

charging at least a portion of said second epoxidation reactor effluent to said ethylene oxide absorber used for separating said second epoxidation reactor effluent into a third recycle stream, having a fifth carbon dioxide concentration, and a second ethylene oxide stream;

dividing said third recycle stream into a second split portion, if any, and a second remaining portion;

charging at least a portion of said second remaining portion to said carbon dioxide removal system as said carbon dioxide-containing feed gas to yield as said carbon dioxide depleted gas stream a fourth recycle stream, having a sixth carbon dioxide concentration, and to yield as said carbon dioxide gas stream a second carbon dioxide vent stream; and combining at least a portion of said second split portion, if any, and at least a portion of said fourth recycle stream with oxygen and ethylene to thereby form said second reactor feed.

15. A method as recited in claim 14, wherein said lean solvent comprises an aqueous solution of alkali metal carbonate.

16. A method as recited in claim 15, further comprising adding an activator to said aqueous solution of alkali metal carbonate.

17. A method as recited in claim 16, further comprising: providing a second carbon dioxide absorber operatively connected in parallel with said carbon dioxide absorber wherein said second carbon dioxide absorber is capable of receiving at least a portion of said second remaining portion and contacting therewith said lean solvent to thereby provide at least a portion of said fourth recycle stream.

18. A method as recited in claim 16, further comprising: modifying the internals of said carbon dioxide absorber to thereby provide enhanced mass transfer and a greater number of theoretical trays and to improve the recovery of carbon dioxide from said at least a portion of said second split portion.

19. A method as recited in claim 16, further comprising: operating said carbon dioxide absorber so as to provide a fourth carbon dioxide concentration less than said first carbon dioxide concentration.

20. A method as recited in claim 14, wherein the fourth carbon dioxide concentration is less than 3 mole percent, based on the total moles of ethylene, oxygen and carbon dioxide in the reactor feed.

21. A method as recited in claim 20, wherein the fourth carbon dioxide concentration is in the range of from 0.1 to less than 2 mole percent, based on the total moles of ethylene, oxygen and carbon dioxide in the reactor feed.

22. A method as recited in claim 21, wherein the fourth carbon dioxide concentration is in the range of from 0.2 to less than 1.5 mole percent, based on the total moles of ethylene, oxygen and carbon dioxide in the reactor feed.

23. A method as recited in claim 14, wherein the silver-based catalyst which includes a rhenium promoter component comprises as a support material an alpha alumina, the amount of silver is in the range of from 1 to 40 weight percent, and the amount of rhenium is in the range of from 0.1 to 10 micromoles per gram, based on the total weight of catalyst; and wherein the silver-based catalyst that does not contain a rhenium promoter component, or contains a nonpromoting amount of a rhenium component, comprises as a support material an alpha alumina, and the amount of silver is in the range of from 1 to 40 weight percent, based on the total weight of catalyst.

24. A method as recited in claim 14, wherein said first reactor feed comprises ethylene and oxygen, in addition to a concentration of carbon dioxide, and said second reactor feed comprises ethylene and oxygen, in addition to a concentration of carbon dioxide.

25. A process for manufacturing ethylene oxide, comprising manufacturing ethylene oxide by operating an ethylene oxide manufacturing process which has been improved by a method as recited in claim 14.

26. A method of improving the operation of an existing ethylene oxide manufacturing process, said method comprises:

a.) operating an epoxidation reactor system by:

charging a first reactor feed, comprising ethylene and oxygen and having a first carbon dioxide concentration, to said epoxidation reactor system comprising an epoxidation reactor containing a first volume of high activity epoxidation catalyst;

yielding from said epoxidation reactor system a first epoxidation reactor effluent;

b.) replacing at least a portion of said first volume of high activity epoxidation catalyst by:

removing from said epoxidation reactor at least a portion of said first volume of high activity epoxidation catalyst and replacing therewith a replacement charge of a second volume of a high selectivity epoxidation catalyst to provide a modified epoxidation reactor system;

c.) operating said modified epoxidation reactor system by:

charging a second reactor feed, comprising ethylene and oxygen and having a fourth carbon dioxide concentration which is lower than said first carbon dioxide concentration, to said modified epoxidation reactor system having said replacement charge; and yielding from said modified epoxidation reactor system a second epoxidation reactor effluent.

27. A method as recited in claim 26, wherein the fourth carbon dioxide concentration is less than 3 mole percent, based on the total moles of ethylene, oxygen and carbon dioxide in the reactor feed.

28. A method as recited in claim 27, wherein the fourth carbon dioxide concentration is in the range of from 0.1 to less than 2 mole percent, based on the total moles of ethylene, oxygen and carbon dioxide in the reactor feed.

29. A method as recited in claim 28, wherein the fourth carbon dioxide concentration is in the range of from 0.2 to less than 1.5 mole percent, based on the total moles of ethylene, oxygen and carbon dioxide in the reactor feed.

30. A method as recited in claim 26, wherein the high selectivity epoxidation catalyst is a silver-based catalyst which includes a rhenium promoter component, and the high activity catalyst is a silver-based catalyst that does not contain a rhenium promoter component, or contains a non-promoting amount of a rhenium component.

31. A method as recited in claim 30, wherein the high selectivity epoxidation catalyst comprises as a support material an alpha alumina, the amount of silver is in the range of from 1 to 40 weight percent, and the amount of rhenium is in the range of from 0.1 to 10 micromoles per gram, based on the total weight of catalyst; and wherein the high activity catalyst comprises as a support material an alpha alumina, and the amount of silver is in the range of from 1 to 40 weight percent, based on the total weight of catalyst.

32. A process for manufacturing ethylene oxide, comprising manufacturing ethylene oxide by operating an ethylene oxide manufacturing process which has been improved by a method as recited in claim 26.

33. A method of improving the operation of an existing ethylene oxide manufacturing process, said method comprises:
   a.) operating an epoxidation reactor system by:
   charging a first reactor feed, comprising ethylene and oxygen and having a first carbon dioxide concentration, to said epoxidation reactor system comprising an epoxidation reactor containing a first volume of a silver-based catalyst that does not contain a rhenium promoter component, or contains a nonpromoting amount of a rhenium component;
   yielding from said epoxidation reactor system a first epoxidation reactor effluent;
   b.) replacing at least a portion of said first volume of said silver-based catalyst by:
   removing from said epoxidation reactor at least a portion of said first volume of said silver-based catalyst that does not contain a rhenium promoter component, or contains a nonpromoting amount of a rhenium component, and replacing therewith a replacement charge of a second volume of a silver-based catalyst which includes a rhenium promoter component, to provide a modified epoxidation reactor system;
   c.) operating said modified epoxidation reactor system by:
   charging a second reactor feed, comprising ethylene and oxygen and having a fourth carbon dioxide concentration which is lower than said first carbon dioxide concentration, to said modified epoxidation reactor system having said replacement charge; and
   yielding from said modified epoxidation reactor system a second epoxidation reactor effluent.

34. A method as recited in claim 33, wherein the fourth carbon dioxide concentration is less than 3 mole percent, based on the total moles of ethylene, oxygen and carbon dioxide in the reactor feed.

35. A method as recited in claim 34, wherein the fourth carbon dioxide concentration is in the range of from 0.1 to less than 2 mole percent, based on the total moles of ethylene, oxygen and carbon dioxide in the reactor feed.

36. A method as recited in claim 35, wherein the fourth carbon dioxide concentration is in the range of from 0.2 to less than 1.5 mole percent, based on the total moles of ethylene, oxygen and carbon dioxide in the reactor feed.

37. A method as recited in claim 33, wherein the high selectivity epoxidation catalyst comprises as a support material an alpha alumina, the amount of silver is in the range of from 1 to 40 weight percent, and the amount of rhenium is in the range of from 0.1 to 10 micromoles per gram, based on the total weight of catalyst; and wherein the high activity catalyst comprises as a support material an alpha alumina, and the amount of silver is in the range of from 1 to 40 weight percent, based on the total weight of catalyst.

38. A process for manufacturing ethylene oxide, comprising manufacturing ethylene oxide by operating an ethylene oxide manufacturing process which has been improved by a method as recited in claim 33.

\* \* \* \* \*